(12) United States Patent
Lee et al.

(10) Patent No.: US 10,987,293 B2
(45) Date of Patent: Apr. 27, 2021

(54) COMPOSITION FOR SKIN EXTERNAL APPLICATION

(71) Applicant: DR. RAYMOND LABORATORIES, INC., Englewood Cliffs, NJ (US)

(72) Inventors: Sin Hee Lee, Daejeon (KR); Byeong Deog Park, Daejeon (KR)

(73) Assignee: DR. RAYMOND LABORATORIES, INC., Englewood Cliffs, NJ (US)

( * ) Notice: Subject to any disclaimer, the term of this patent is extended or adjusted under 35 U.S.C. 154(b) by 0 days.

(21) Appl. No.: 16/647,001

(22) PCT Filed: Feb. 27, 2019

(86) PCT No.: PCT/KR2019/002367
§ 371 (c)(1),
(2) Date: Mar. 12, 2020

(87) PCT Pub. No.: WO2019/172572
PCT Pub. Date: Sep. 12, 2019

(65) Prior Publication Data
US 2020/0276096 A1    Sep. 3, 2020

(30) Foreign Application Priority Data

Mar. 9, 2018  (KR) .................. 10-2018-0027793
Feb. 21, 2019  (KR) .................. 10-2019-0020308

(51) Int. Cl.
| | |
|---|---|
| *A61K 8/41* | (2006.01) |
| *A61K 8/42* | (2006.01) |
| *A61K 8/63* | (2006.01) |
| *A61K 31/133* | (2006.01) |
| *A61K 31/16* | (2006.01) |
| *A61K 31/56* | (2006.01) |
| *A61Q 19/00* | (2006.01) |

(52) U.S. Cl.
CPC .................. *A61K 8/41* (2013.01); *A61K 8/42* (2013.01); *A61K 8/63* (2013.01); *A61K 31/133* (2013.01); *A61K 31/16* (2013.01); *A61K 31/56* (2013.01); *A61Q 19/007* (2013.01); *A61K 2800/60* (2013.01)

(58) Field of Classification Search
CPC ... A61K 8/41; A61K 8/42; A61K 8/63; A61K 31/133; A61K 31/16; A61K 31/56; A61K 2800/60; A61Q 19/007
See application file for complete search history.

(56) References Cited

U.S. PATENT DOCUMENTS 6,410,597 B1    6/2002  Bieberich et al.
2012/0089105 A1    4/2012  Jaspers et al.

FOREIGN PATENT DOCUMENTS

| EP | 0875232 A1 | * | 11/1998 | .............. A61Q 5/00 |
| EP | 0968998 A1 | * | 1/2000 | .............. A61P 17/00 |
| EP | 0968998 A1 | * | 1/2000 | .............. A61P 17/00 |
| KR | 101828241 A1 | | 2/2018 | |
| WO | 2017188623 A1 | | 11/2017 | |

OTHER PUBLICATIONS

EP0968998A1, Machine Translation (Year: 2000).*
WO2015147137A1, Machine Translation (Year: 2015).*
Park (Year: 2017).*
Bieberich (Year: 2000).*
Park2003 (Year: 2003).*
Williams et als., Quantitative method for the profiling of the endocannabinoid metabolome by LC-atmospheric pressure chemical ionization—MS. Analytical Chemistry, 2007, vol. 79, No. 15, pp. 5582-5593 (Aug. 1, 2017).

* cited by examiner

*Primary Examiner* — Jeffrey S Lundgren
*Assistant Examiner* — Ibrahim D Bori
(74) *Attorney, Agent, or Firm* — SIMI Law Group, P.C.

(57) ABSTRACT

The present invention relates to a composition for skin external application. Specifically, a composition for skin external application comprising a stably formed lamella liquid crystal phase can be provided according to the present invention. In addition, according to the present invention, the composition can provide excellent skin moisturizing and skin barrier strengthening effects upon application on the skin, as well as act effectively as an agent for a cannabinoid type 1 receptor, such that it is expected that the present invention can provide a very effective effect for treatment or improvement of skin diseases and mental disorders associated with skin diseases.

10 Claims, 6 Drawing Sheets

[FIG. 1]
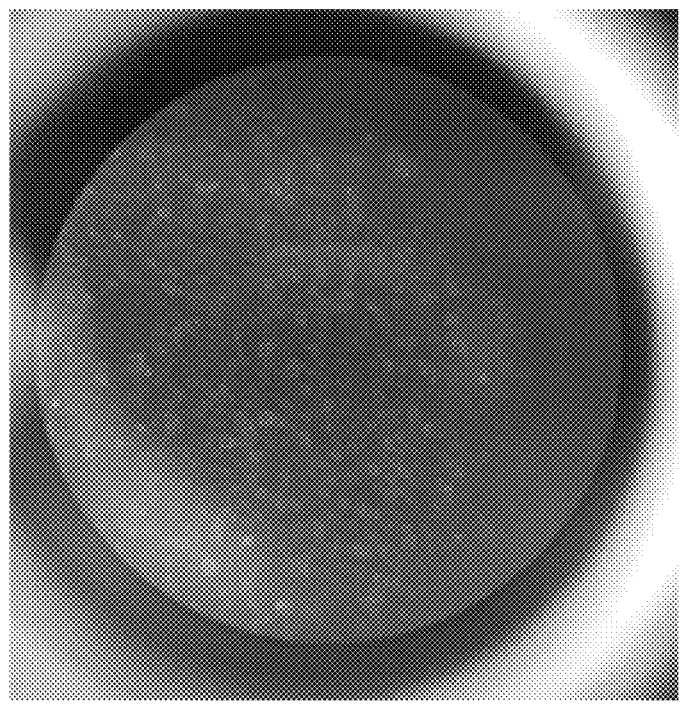
[FIG. 2]
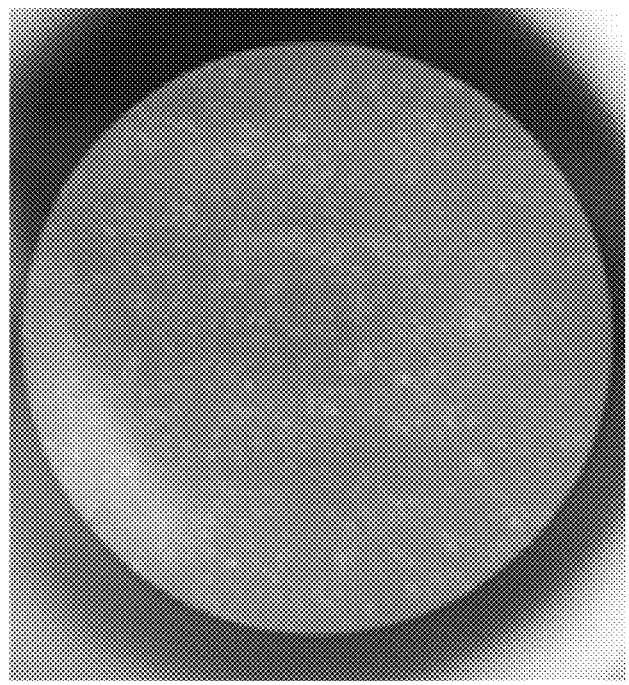

【FIG. 3】
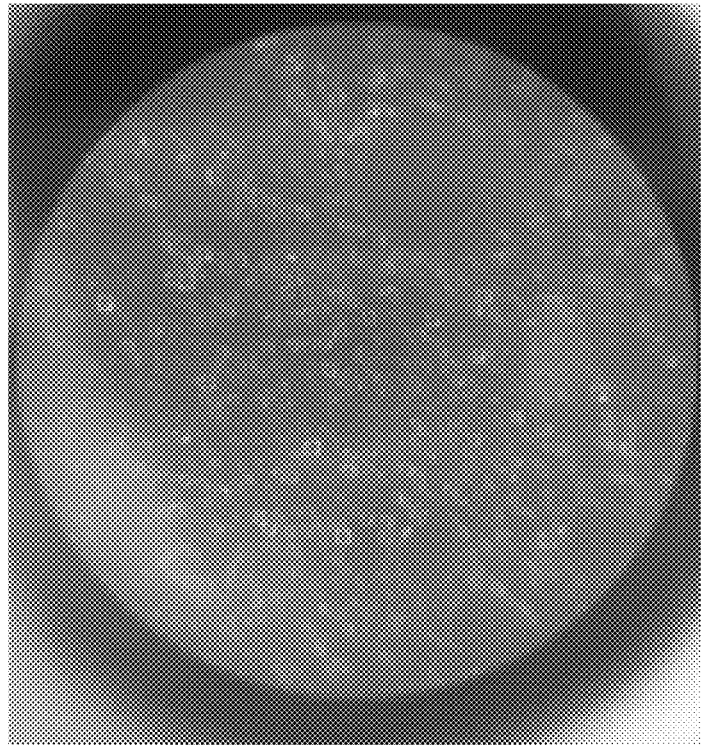
【FIG. 4】
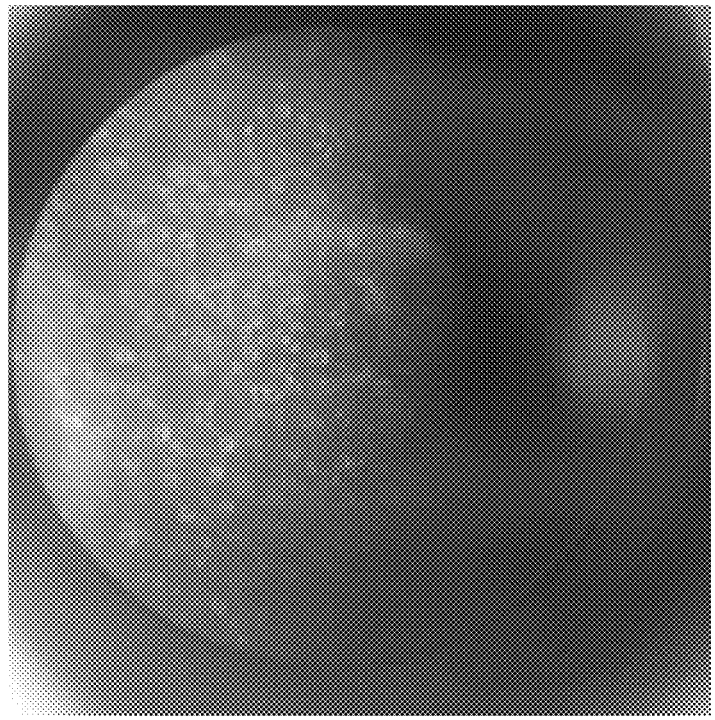

[FIG. 5]
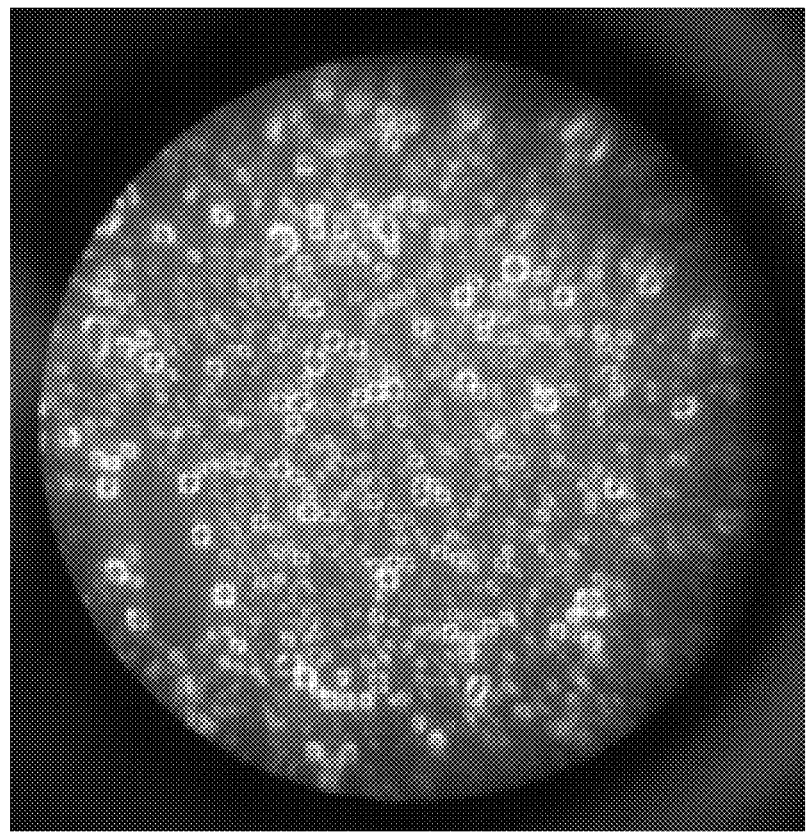

【FIG. 6】
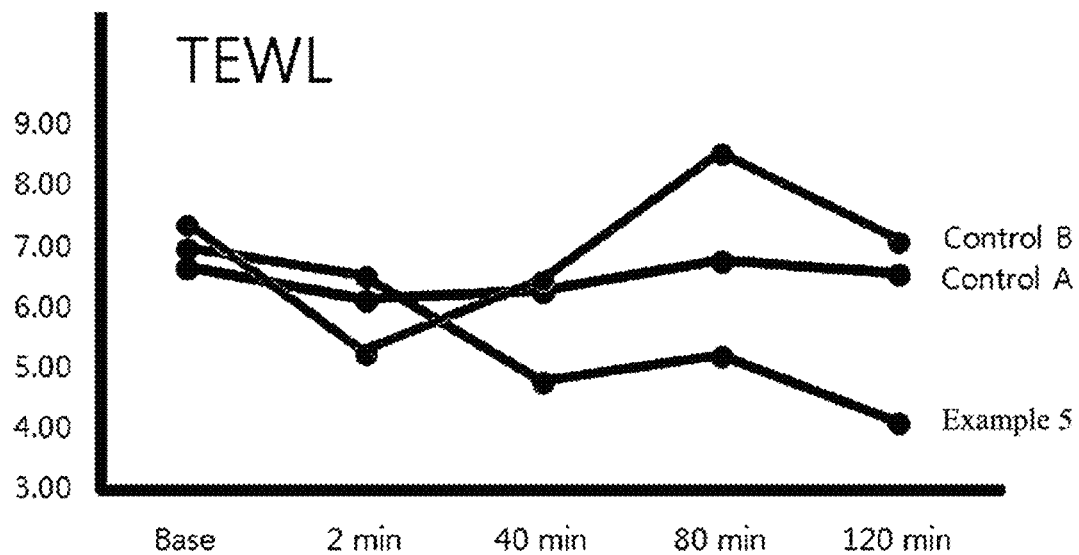
【FIG. 7】
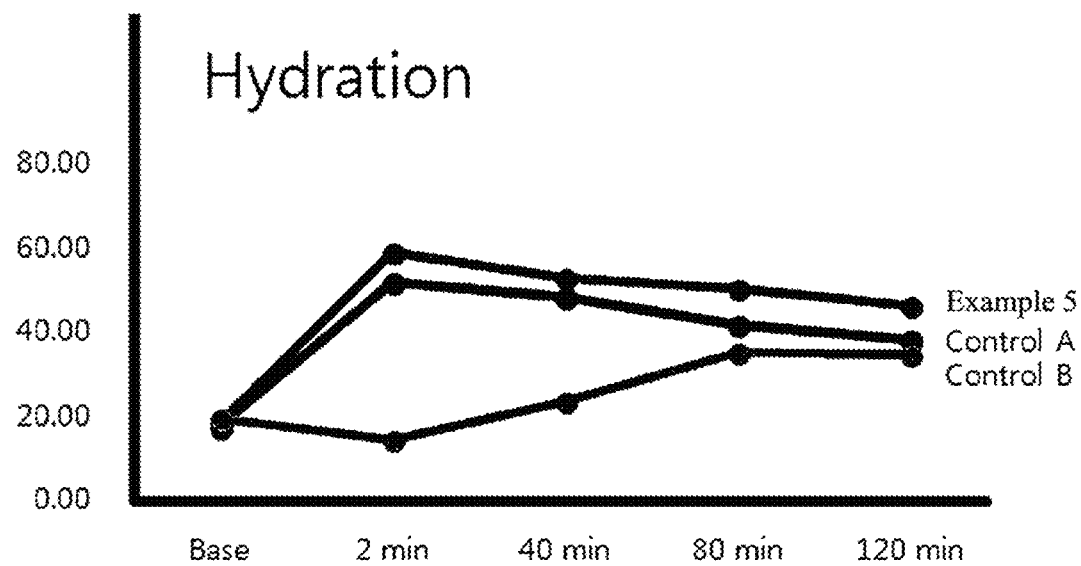

[FIG. 8]
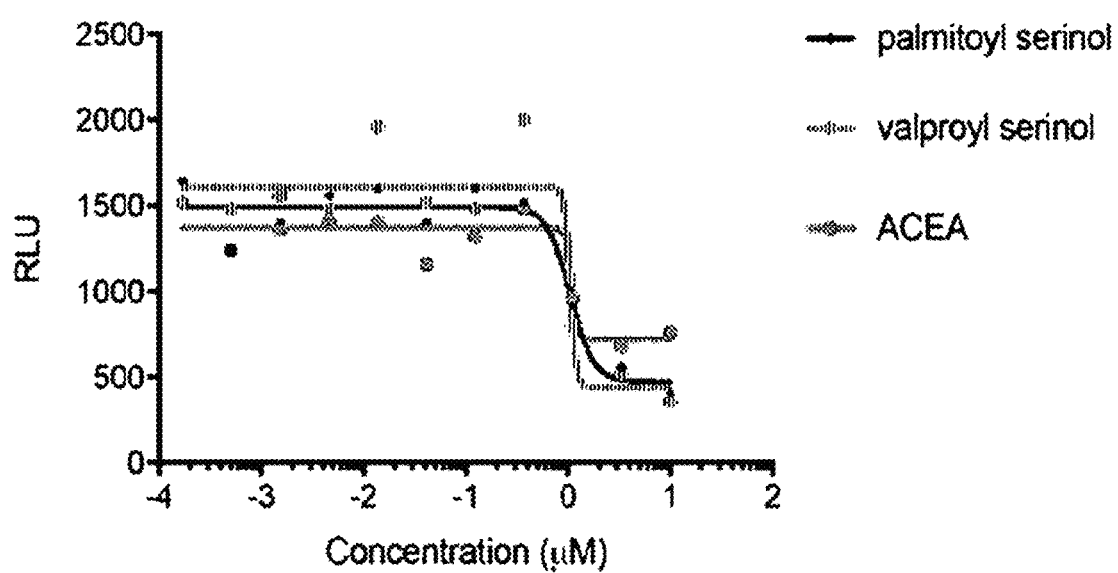

[FIG. 9]
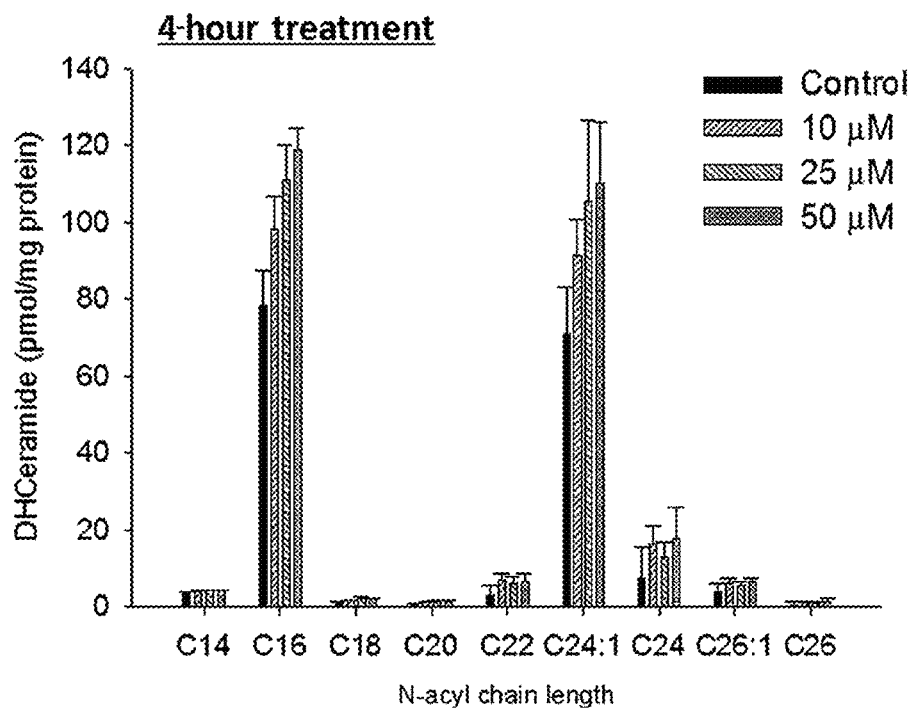
[FIG. 10]
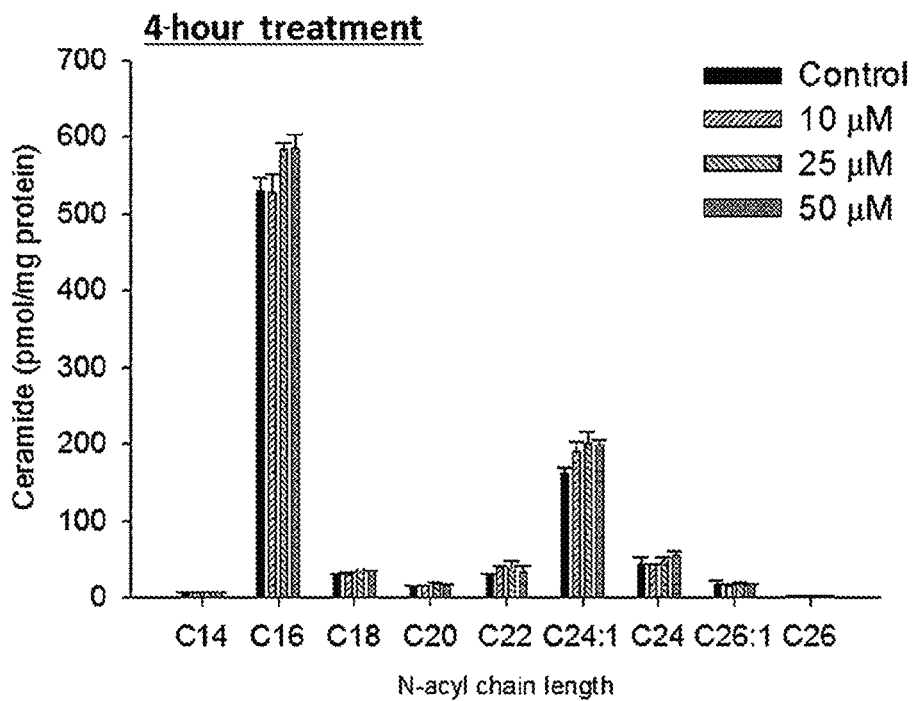

COMPOSITION FOR SKIN EXTERNAL APPLICATION

This application is the National Stage Application PCT/KR2019/002367, filed on Feb. 27, 2019, which claims priority to Korean Patent Application Nos.: KR 10-2018-0027793, filed on Mar. 9, 2018, and KR 10-2019-0020308, filed Feb. 21, 2019, all of which are incorporated by reference for all purposes as if fully set forth.

TECHNICAL FIELD

The present invention relates to a composition for skin external application.

BACKGROUND ART

In recent years, endocannabinoids have come into the spotlight. In 1963, an Israeli chemist, Dr. Raphael Mechoulam, isolated and synthesized delta-9-tetrahydrocannabinol (THC). Afterwards, anandamide (AEA) that is one of the endocannabinoids was first found in 1992 by Dr. Mechoulam's laboratory group, and 2-arachidonoylglycerol (2-AG) that is another one of the endocannabinoids was found between 1994 and 1995 by Shimon Ben-Shabat of the same laboratory group. With the findings, research on receptors continued. As a result, a cannabinoid type 1 receptor that is a receptor of endocannabinoids was found in 1990 by Allyn Howlett and William Devan, and a cannabinoid type 2 receptor was found in 1993 by the researchers of Cambridge University.

In particular, the cannabinoid type 1 receptor is expressed in the brain, cardiovascular tissues, vascular endothelial cells, and the like. Also, it is known that an agonist for a cannabinoid type 1 receptor takes part in the control of higher-order functions of the brain by inhibiting the release of neurotransmitters by the intracellular signaling system through the cannabinoid type receptor, such as regulation of the adenylate cyclase activity, regulation of N- and P/Q-type $Ca^{2+}$ channels, activation of voltage-gated $K^+$ channels, activation of the MAP kinase activity, and the like. Also, the research results report that the cannabinoid type 1 receptor also exists in peripheral tissues, and thus has therapeutic potential as appetite stimulants, anti-emetics, analgesics, glaucoma therapeutic agents, tumor growth suppressors, and preparations for treating neurodegenerative disorders including multiple sclerosis, Alzheimer's disease, and the like. Also, it is known that the endocannabinoid receptors exist in the skin, and, when the agonist acts on the cannabinoid type 1 receptor, the synthesis of ceramide is promoted and the skin barrier function is restored, so that the cannabinoid type 1 receptor has an effect of improving dry skin, itching, or the like.

With this background, it can be expected that, when the agonist for a cannabinoid type 1 receptor is applied similar to the endocannabinoids, it is effective for atopic dermatitis as well as itching, dry skin, and the like, which are associated with the atopic dermatitis. It is supposed that atopic dermatitis or the like is a type of skin disease whose symptoms are worsened by the excessive activities of mast cells, and it develops in complex conjunction with genetic, environmental and immunological factors, and the like even when its exact etiology is not known. In patients having such atopic dermatitis, the mast cells are activated in both an immunoglobulin E-dependent reaction and an immunoglobulin E-independent reaction so that the plasma membrane and vesicular membrane of the cytoplasm are fused to cause degranulation. Also, when various allergens are bound to specific immunoglobulin E (IgE) in the mast cells, the allergens strongly bind to an IgE receptor (FceRI) on surfaces of the mast cells to secrete histamine. As a result, when the activity of the mast cells is suppressed, a level of histamine secreted from the mast cells is reduced, thereby providing suitable efficacy to improve and treat atopic dermatitis. However, most of the conventional techniques for improving and treating atopic dermatitis are to take antihistaminics or use steroid preparations to prevent and relieve itching. However, because these drugs cause side effects such as central nervous system disorders, digestive disorders, somnolence, or the like when one takes or applies the drugs, there is an urgent demand for development of new materials and preparations that may overcome such side effects and have no toxicity.

Also, Non-patent Document 1 shows that a developmental disorder (autism) is examined to be 7.41-fold higher in children having skin diseases such as atopic dermatitis. Specifically, because the children having skin diseases such as atopic dermatitis, and the like often exhibit mental disorders such as attention deficit hyperactivity disorder (ADHD), intermittent explosive disorder, depression, conduct disorder, and the like, it is expected that an agent for skin external application having an excellent skin protection function may be effectively used first to effectively control atopic dermatitis, and then care for the skin whose skin barrier functions are attenuated, which exhibits a developmental disorder, attention deficit hyperactivity disorder, intermittent explosive disorder, depression, conduct disorder, and the like. In particular, recent research results report the abnormalities in the endocannabinoid system even in autistic patients. Non-patent Document 2 reports that the autism symptoms are improved when autistic patients are allowed to take palmitoyl ethanolamide (PEA) that is one of the cannabinoid type 1 receptor agonists. With such a research background, it is expected that development of a material capable of acting as the cannabinoid type 1 receptor agonist may provide an effective effect in treating or improving atopic dermatitis, or dry skin, itching, and the like associated with the atopic dermatitis and may also provide an effective effect in caring for the skins of patients having mental disorders who has a higher chance of developing atopic dermatitis, such as autism, a hyperactivity disorder, and the like.

DISCLOSURE

Technical Problem

An object of the present invention is to provide a composition for skin external application capable of providing an excellent moisturizing effect and effectively regenerating a damaged skin barrier at the same time.

Specifically, an object of the present invention is to provide a composition for skin external application capable of acting as a selective agonist for a cannabinoid type 1 receptor.

Specifically, an object of the present invention is to provide a composition for skin external application capable of expressing an effective effect in improving the skin with cannabinoid type 1 receptor-related skin diseases and diseases associated with the skin diseases by activating the cannabinoid type 1 receptor.

Specifically, an object of the present invention is to provide a composition for skin external application for normally regenerating a skin barrier to assist the normal skin protection function.

Specifically, an object of the present invention is to provide a composition for skin external application, which is suitable for treatment or improvement of skin diseases such as atopic dermatitis, and the like, and mental disorders associated with skin whose skin barrier functions are attenuated.

Technical Solution

To solve the above problems, in one general aspect, a composition for skin external application includes a serinol-based compound selected from palmitoyl serinol, valproyl serinol, and the like.

The composition for skin external application according to an exemplary embodiment of the present invention may further include a sterol-based compound, a higher fatty acid, a higher fatty acid alcohol, and the like.

The composition for skin external application according to an exemplary embodiment of the present invention may include 1 to 10 parts by weight of the sterol-based compound, 5 to 30 parts by weight of the higher fatty acid, and 10 to 50 parts by weight of the higher fatty acid alcohol, based on 1 part by weight of the serinol-based compound.

The composition for skin external application according to an exemplary embodiment of the present invention may form Maltese cross liquid crystals.

The composition for skin external application according to an exemplary embodiment of the present invention may further include a ceramide selected from ceramide 1, ceramide 3, ceramide 3B, ceramide 4, ceramide 6, myristoyl/palmitoyl oxostearamide/arachamide MEA (Brand Name: PC-9S), hydroxypropylbispalmitamide MEA (Brand Name: PC-104), hydroxypropylbispalmitamide MEA (Brand Name: PC-102), dihydroxyisopropyl palmoylpalmamide, and the like.

In the composition for skin external application according to an exemplary embodiment of the present invention, the ceramide may be included at 0.01 to 10 parts by weight, based on 1 part by weight of the serinol-based compound.

The composition for skin external application according to an exemplary embodiment of the present invention may be for moisturizing the skin or strengthening a skin barrier.

The composition for skin external application according to an exemplary embodiment of the present invention may be for improving a skin disease.

The composition for skin external application according to an exemplary embodiment of the present invention may be a pharmaceutical composition for treating or preventing a skin disease.

In the composition for skin external application according to an exemplary embodiment of the present invention, the skin disease may be atopic dermatitis or the like.

The composition for skin external application according to an exemplary embodiment of the present invention may be for treating or improving a mental disorder associated with the skin disease.

In the composition for skin external application according to an exemplary embodiment of the present invention, the mental disorder may be attention deficit hyperactivity disorder, intermittent explosive disorder, depression, conduct disorder, or the like.

The composition for skin external application according to an exemplary embodiment of the present invention may be for treating or improving a mental disorder.

In another general aspect, a method for improving a skin disease, a dermatological disorder, or a mental disorder associated with the skin disease or the dermatological disorder by applying the composition for skin external application, which includes a serinol-based compound selected from palmitoyl serinol and valproyl serinol, on the skin is provided.

In still another general aspect, a method for preventing or treating a skin disease, a dermatological disorder, or a mental disorder associated with the skin disease or the dermatological disorder by applying the composition for skin external application, which includes a serinol-based compound selected from palmitoyl serinol and valproyl serinol, on the skin is provided.

Advantageous Effects

According to the present invention, a composition for skin external application including a stably formed lamella liquid crystal phase can be provided, thereby providing excellent skin moisturizing and skin barrier strengthening effects upon application on the skin. Specifically, according to the present invention, the composition for skin external application can help to promote differentiation of skin keratinocytes to reduce the stratum corneum and normally regenerate a skin barrier damaged by lipid components provided in a stably formed lamella liquid crystal phase to aid in providing a normal skin protection function.

Also, according to the present invention, because the composition for skin external application acts as an effective agonist for a cannabinoid type 1 receptor, the composition for skin external application can be useful in preventing, improving, or treating a cannabinoid type 1 receptor-mediated skin disease. Further, according to the present invention, the composition for skin external application can be suitable for preventing, improving, or treating a skin disease such as atopic dermatitis, or the like, and a mental disorder associated with the skin disease, for example, attention deficit hyperactivity disorder, intermittent explosive disorder, depression, conduct disorder, or the like.

DESCRIPTION OF DRAWINGS

FIG. 1 is an image of liquid crystals (polarizing microscope image; magnification: ×400) formed from a composition for skin external application prepared in Example 1 of the present invention.

FIG. 2 is an image of liquid crystals (polarizing microscope image; magnification: ×400) formed from a composition for skin external application prepared in Example 2 of the present invention.

FIG. 3 is an image of liquid crystals (polarizing microscope image; magnification: ×400) formed from a composition for skin external application prepared in Example 3 of the present invention.

FIG. 4 is an image of liquid crystals (polarizing microscope image; magnification: ×400) formed from a composition for skin external application prepared in Example 4 of the present invention.

FIG. 5 is an image of liquid crystals (polarizing microscope image; magnification: ×400) formed from a composition for skin external application prepared in Example 5 of the present invention.

FIG. 6 is a graph illustrating the skin moisturizing effects of the composition for skin external application prepared in Example 5 of the present invention and a control material (Vaseline).

FIG. 7 is a graph illustrating the skin barrier strengthening effects of the composition for skin external application prepared in Example 5 of the present invention and the control material (Vaseline).

FIG. 8 is a graph illustrating the efficacies of the serinol-based compounds according to the present invention and ACEA that is a cannabinoid type 1 receptor, all of which are used as cannabinoid type 1 receptor agonists.

FIG. 9 is a graph illustrating the experimental results showing that the serinol-based compound according to the present invention increases the biosynthesis of dihydroceramide in keratinocytes.

FIG. 10 is a graph illustrating the experimental results showing that the serinol-based compound according to the present invention increases the biosynthesis of ceramide in keratinocytes.

BEST MODE

Hereinafter, a composition for skin external application according to the present invention will be described in detail. In this case, unless otherwise defined, the technical and scientific terms used herein have the same meaning as commonly understood by one of ordinary skill in the art to which the present invention pertains. In the following description, a description of known functions and configurations, which may unnecessarily obscure the subject matter of the present invention, will be omitted.

The present inventors have repeatedly conducted research on a new preparation to optimize the skin protection function, and found that very stable liquid crystals may be formed when a serinol-based compound is used, and also have excellent long-term stability at a high temperature. Also, the present inventors have found that the serinol-based compound is useful as an agonist for a cannabinoid type 1 receptor.

Specifically, the composition for skin external application according to the present invention may effectively regenerate a skin barrier damaged by lipid components in a stably formed lamella liquid crystal phase. That is, when the composition for skin external application according to the present invention is applied on the skin, the composition for skin external application restores a skin barrier function to exhibit a remarkable skin moisturizing effect. Also, since the composition for skin external application according to the present invention has a structure similar to lipid-based molecules such as lipid components, and the like, the composition for skin external application may form a lamella liquid crystal phase, and has an outstanding affinity for the skin, thereby greatly improving absorption of the serinol-based compound. Also, the composition for skin external application according to the present invention may impart a long-lasting effect due to the lipid components of the stably supplied lamella liquid crystal phase, thereby imparting a more improved moisturizing effect.

Specifically, because the composition for skin external application according to the present invention may act as an agonist or regulator for a cannabinoid type 1 receptor without any side effects, the composition for skin external application may have an effective effect in preventing, improving, or treating a cannabinoid type 1 receptor-mediated skin disease, and the like.

Hereinafter, the composition for skin external application according to the present invention will be described in detail.

An aspect of the present invention relates to a composition for skin external application including a serinol-based compound selected from palmitoyl serinol and valproyl serinol. In this case, it is reasonable that palmitoyl serinol or valproyl serinol may be used alone or may be used in the form of a mixture thereof in the composition for skin external application. Specific examples of the serinol-based compound are as described below.

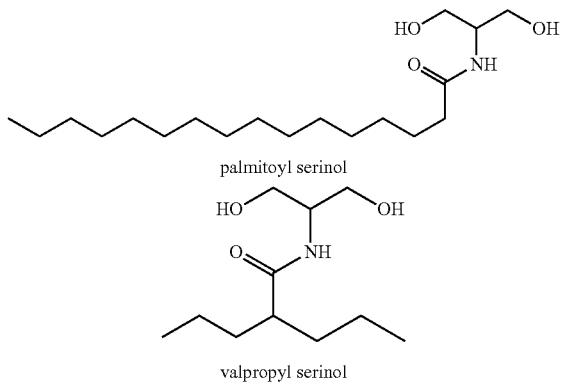

palmitoyl serinol valpropyl serinol

The composition for skin external application according to the present invention may be specifically a cosmetic composition or a pharmaceutical composition, and may be more specifically a cosmetic composition.

The composition for skin external application according to an exemplary embodiment of the present invention may include 0.01 to 5% by weight of the serinol-based compound and the balance of water, based on the total weight of the composition for skin external application. The composition for skin external application may specifically include 0.01 to 3% by weight of the serinol-based compound and the balance of water, and may more specifically include 0.1 to 2% by weight of the serinol-based compound and the balance of water.

As one example, when the serinol-based compound is used in the form of a mixture, the valproyl serinol may be used at 0.01 to 1 part by weight, based on 1 part by weight of the palmitoyl serinol.

As one example, when the serinol-based compound is used in the form of a mixture, the valproyl serinol may be used at more than 1 part by weight and 100 parts by weight or less, based on 1 part by weight of the palmitoyl serinol.

As described above, the composition for skin external application according to an exemplary embodiment of the present invention may be combined with the lipid components for forming liquid crystals to provide a stable lamella liquid crystal phase.

Specifically, the composition for skin external application may provide a very stable lamella liquid crystal phase because the lipid components such as a sterol-based compound, a higher fatty acid, a higher fatty acid alcohol, and the like are combined with the serinol-based compound selected from palmitoyl serinol, valproyl serinol, and the like.

The liquid crystals formed by the aforementioned combination may be absorbed into the skin with an outstanding affinity for the skin, thereby enhancing uniformity and solidity of intercellular lipids. Therefore, the composition for skin external application may realize a more improved moisturizing effect, and may effectively regenerate a skin barrier damaged by the lipid components provided in a stably formed lamella liquid crystal phase. In this case, an abnormality in skin condition caused by the damaged skin barrier is referred to as a dermatological disorder. Such a dermatological disorder may include an abnormality in skin condition caused by the damaged skin barrier due to skin diseases as will be described below.

As one example, the sterol-based compound may include one or two or more selected from cholesterol, phytosterol, 3b-[N—(N',N'-dimethylaminoethane)-carbamyl]cholesterol (DC-Chol), stigmasterol, campesterol, sitosterol, ergosterol, lanosterol, dinosterol, gorgosterol, avenasterol, saringosterol, fucosterol, cholesteryl hemisuccinate, cholesteryl benzoate, cholesteryl oleate, cholesteryl oleyl carbonate, cholesteryl isostearate, cholesteryl linoleate, cholesteryl acetate, cholesteryl palmitate, cholesteryl stearate, cholesteryl chloride, cholesteryl nonanoate, cholesteryl arachidonate, and the like.

As one example, the higher fatty acid may be a higher fatty acid having 10 to 25 carbon atoms. Specifically, the higher fatty acid may include one or two or more selected from oleic acid, linoleic acid, behenic acid, arachidonic acid, stearic acid, palmitic acid, myristic acid, lauric acid, and the like.

As one example, the higher fatty acid alcohol may be a higher fatty acid alcohol having 10 to 25 carbon atoms. Specifically, the higher fatty acid alcohol may include one or two or more selected from cetearyl alcohol, stearyl alcohol, cetostearyl alcohol, behenyl alcohol, and the like.

In the composition for skin external application according to an exemplary embodiment of the present invention, the aforementioned serinol-based compound and lipid components may be used in amounts used for forming liquid crystals. Specifically, the lipid components including 1 to 10 parts by weight of the sterol-based compound; 5 to 30 parts by weight of the higher fatty acid; and 10 to 50 parts by weight of the higher fatty acid alcohol, based on 1 part by weight of the serinol-based compound, may be used.

As one example, in the composition for skin external application, the lipid components including 3 to 10 parts by weight of the sterol-based compound; 8 to 20 parts by weight of the higher fatty acid; and 20 to 50 parts by weight of the higher fatty acid alcohol, based on 1 part by weight of the serinol-based compound, may be used.

As one example, in the composition for skin external application, the lipid components including 3 to 8 parts by weight of the sterol-based compound; 10 to 20 parts by weight of the higher fatty acid; and 20 to 40 parts by weight of the higher fatty acid alcohol, based on 1 part by weight of the serinol-based compound, may be used.

The liquid crystals formed from the composition for skin external application according to an exemplary embodiment of the present invention may be Maltese cross liquid crystals. In this case, the Maltese cross liquid crystals may be in the form of a single layer or multiple layers.

As the shape of the liquid crystals is realized, more stable liquid crystals may be formed, thereby preventing a precipitation phenomenon of the lipid components. Also, the liquid crystals may easily penetrate the skin, thereby further improving uniformity and solidity of the intercellular lipids.

The composition for skin external application according to an exemplary embodiment of the present invention may form liquid crystals with compositions similar to the components of intercellular lipids. In this case, the liquid crystals may be applied on the skin to form a Maltese cross liquid crystal film on the skin. That is, when the composition for skin external application is applied on the skin, the composition for skin external application may provide an immediate moisturizing effect as well as a continuous moisturizing effect with the realization of a long-lasting effect. Therefore, the composition for skin external application has an effect of improving and treating a skin disease such as xeroderma, atopic dermatitis, and the like.

As one example, in the composition for skin external application, the Maltese cross liquid crystals may have a size ranging from 0.5 to 10 μm. Specifically, the Maltese cross liquid crystals may have a size ranging from 0.5 to 8 μm, and more specifically a size ranging from 0.5 to 4 μm.

Also, the composition for skin external application according to an exemplary embodiment of the present invention may further include a ceramide, thereby further enhancing stability of the liquid crystals.

As one example, the ceramide may be selected from a natural ceramide, a synthetic ceramide, and a pseudoceramide. Specifically, the ceramide may include one or two or more selected from ceramide 1, ceramide 3, ceramide 3B, ceramide 4, ceramide 6, myristoyl/palmitoyl oxostearamide/arachamide MEA (Brand Name: PC-9S), hydroxypropylbispalmitamide MEA (Brand Name: PC-104), hydroxypropylbispalmitamide MEA (Brand Name: PC-102), dihydroxyisopropyl palmoylpalmamide, and the like.

In the composition for skin external application according to an exemplary embodiment of the present invention, the ceramide may be included at 0.01 to 10 parts by weight, based on 1 part by weight of the serinol-based compound. Specifically, the ceramide may be included at 0.05 to 8 parts by weight, and more specifically 0.1 to 6 parts by weight.

As one example, the composition for skin external application may include 0.01 to 5% by weight of the serinol-based compound, based on the total weight of the composition for skin external application. In this case, the serinol-based compound and the ceramide may be mixed at a ratio of 1:0.1 to 1:6 (wt:wt).

Hereinafter, specific aspects of the composition for skin external application according to the present invention will be described.

The composition for skin external application according to an exemplary embodiment of the present invention may be a cosmetic composition for moisturizing the skin or strengthening a skin barrier. The cosmetic composition does not cause side effects on the skin, such as epidermal hyperplasia, and the like, and also has an improved skin moisturizing effect and an improved effect of effectively regenerating a damaged skin barrier.

Also, the composition for skin external application according to an exemplary embodiment of the present invention may be a cosmetic composition for improving a cannabinoid type 1 receptor-mediated skin disease such as atopic dermatitis, and the like. The cosmetic composition for improving a skin disease has an improved skin moisturizing effect. Also, the cosmetic composition for improving a skin disease exhibits a remarkable effect on the skin disease since the cosmetic composition effectively improves the damaged skin barrier to maximize the skin moisturizing effect. Further, the cosmetic composition for improving a skin disease exhibits an effect of improving a mental disorder associated with the skin whose skin barrier functions are attenuated.

Further, the composition for skin external application according to an exemplary embodiment of the present invention may be safely used without any toxicity and side effects to treat and improve a skin disease and a mental disorder associated with the skin disease.

Specifically, the cosmetic composition may be formulated into conventional emulsion formulations, solubilizing formulations, and the like using the preparation methods commonly known in the art.

As one example, the cosmetic composition may be formulated into a formulation selected from the group consisting of a lotion, a toner, a face lotion, an eye cream, a nourishing cream, a massage cream, a cleansing cream, a cleansing foam, a cleansing water, a powder, an essence, a pack, and the like.

Also, the cosmetic composition may properly further include an additional additive according to a purpose. As one example, the additive may include one or more aqueous additives selected from a stabilizing agent, an emulsifying agent, a thickening agent, a moisturizing agent, a liquid crystal film reinforcing agent, a pH control agent, an antibacterial agent, a water-soluble polymer, a coating agent, a chelating agent, an amino acid, an organic amine, a polymeric emulsion, a pH adjuster, a skin nutrient, an antioxidant, an antioxidant aid, a preservative, a fragrance, and the like; and one or more oily additives such as an oil, a wax, a hydrocarbon oil, a higher fatty acid oil, a higher alcohol, a synthetic ester oil, and a silicone oil; and the like.

In this case, each of the additives may be included at 0.001 to 20% by weight, and specifically included at 0.01 to 10% by weight or 0.05 to 10% by weight, based on the total weight of the composition, but the present invention is not limited thereto.

The composition for skin external application according to an exemplary embodiment of the present invention may be a pharmaceutical composition for treating, preventing, or improving a skin disease. That is, the composition for skin external application exhibits a remarkable effect on the skin disease since the composition effectively regenerates the damaged skin barrier to optimize the skin protection function. Further, the composition for skin external application exhibits an effect in treating or improving the skin with a mental disorder associated with the skin whose skin barrier functions are attenuated.

Also, the composition for skin external application according to an exemplary embodiment of the present invention acts as an agonist for a cannabinoid type 1 receptor to suppress the overexpressed cannabinoid type 1 receptor or effectively suppress the activity of mast cells, thereby exhibiting an effective effect in treating and preventing a skin disease.

Specifically, the composition for skin external application according to an exemplary embodiment of the present invention may be a pharmaceutical composition for treating or improving atopic dermatitis. Also, the pharmaceutical composition may exhibit an effect on skin diseases caused by attenuation of the skin barrier functions, such as psoriasis, contact dermatitis, eczematous dermatitis, actinic dermatitis, seborrheic dermatitis, dermatitis herpetiformis, lichen planus, lichen sclerosus, pyoderma gangrenosum, pemphigus, epidermolysis bullosa, systemic sclerosis, leprosy, or the like.

Also, the composition for skin external application according to an exemplary embodiment of the present invention may be a pharmaceutical composition for treating or improving a mental disorder associated with the skin disease.

As one example, the mental disorder may be a developmental disorder, attention deficit hyperactivity disorder, intermittent explosive disorder, depression, conduct disorder, or the like.

In addition, the composition for skin external application according to an exemplary embodiment of the present invention may be a pharmaceutical composition for treating or improving a mental disorder.

Further, the composition for skin external application according to an exemplary embodiment of the present invention may be a pharmaceutical composition for treating or improving a neurodegenerative disease such as Alzheimer's disease, and the like, which may be a cannabinoid type 1 receptor-related disease.

Accordingly, it is expected that the pharmaceutical composition may exhibit an outstanding effect on all types of skin diseases, mental disorders, and the like, which corresponds to an improvement or treatment with the realization of the aforementioned effects according to the present invention, and may also give a synergistic effect to a prevention and improvement of cannabinoid type 1 receptor-mediated diseases associated with the skin diseases and mental disorders.

Specifically, the pharmaceutical composition may be formulated into a formulation including a pharmaceutically available carrier using the preparation methods commonly known in the art.

As one example, the pharmaceutical composition may be formulated into a formulation selected from the group consisting of a lotion, an ointment, a gel, a cream, a patch, a spray, and the like.

Also, the pharmaceutical composition may properly include an additional pharmaceutically available carrier according to a purpose. As one example, the additional pharmaceutically available carrier may be lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, or mineral oil, but the present invention is not limited thereto. In addition to the carriers, the pharmaceutical composition may also further include a carrier such as a lubricant, a wetting agent, a sweetening agent, a flavoring agent, an emulsifying agent, a suspending agent, a preservative, or the like.

In this case, each of the carriers may be included at 0.001 to 20% by weight, and specifically included at 0.01 to 10% by weight or 0.05 to 10% by weight, based on the total weight of the composition, but the present invention is not limited thereto.

Also, the present invention provides a method for improving a skin disease, a dermatological disorder, or a mental disorder associated with the skin disease or the dermatological disorder by applying the composition for skin external application, which includes a serinol-based compound selected from palmitoyl serinol and valproyl serinol, on the skin.

Further, the present invention provides a method for preventing or treating a skin disease, a dermatological disorder, or a mental disorder associated with the skin disease or the dermatological disorder by applying the composition for skin external application, which includes a serinol-based compound selected from palmitoyl serinol and valproyl serinol, on the skin.

(Evaluation Method)

1. Skin Moisturizing Effect

To evaluate a moisturizing ability of each of the samples (Examples and Comparative Examples), a short-term moisturizing test was performed. In this case, the control materials, that is, a formulation forming no Maltese cross liquid crystals (Comparative Example 1) and Vaseline, were used as Controls A and B, respectively.

Left and right parts of the forearm of each of subjects were washed with soap, and the skin was then adapted to a temperature of approximately 20° C. and a humidity of approximately 40%. At the same time, a skin smoothing effect was evaluated using a moisturizing ability test. Test regions were determined as the left and right inner parts of the forearm in a rectangle with a size of 4×3 cm$^2$, and the capacitance of the skin surface was repeatedly measured three times using a corneometer (CM825). 24 µL (2 mg/cm$^2$) of each of the samples was applied on the test regions.

After 2 minutes, 40 minutes, 80 minutes, and 120 minutes of the application, the capacitance of the skin surface was repeatedly measured three times in the same manner as performed prior to the application. An average value of the capacitances repeatedly measured three times was calculated. Thereafter, the value is shown in FIG. 7 below.

2. Skin Barrier Strengthening Effect 2-1. To evaluate an effect of strengthening the skin barrier function of each of the samples (Examples and Comparative Examples), transepidermal water loss was measured. In this case, the control materials, that is, a formulation forming no Maltese cross liquid crystals (Comparative Example 1) and Vaseline, were used as Controls A and B, respectively.

The transepidermal water loss (TEWL) was measured using Tewameter TM210 (Courage & Khazaka Electronic GmbH, Germany). A method for applying each of the samples onto a test region was followed by the evaluation of the moisturizing ability.

The values measured by the aforementioned method are shown in FIG. 6 below.

To evaluate skin barrier stabilities of the applied regions, the transepidermal water loss was also measured while repeatedly removing the stratum corneum from each of the applied regions using a D-Squame tape (CuDerm Corporation, Dallas, Tex., USA).

2-2. An effect of each of the palmitoyl serinol and valproyl serinol samples on the biosynthesis of long-chain ceramide was determined as follows.

Specifically, keratinocytes were treated with each of the samples (at concentrations of 10, 25, and 50 µg/mL) while being cultured in a 1000 culture dish, and then cultured for 24 hours. When the culture was terminated, the medium was removed. Thereafter, quantitative analyses of the long-chain ceramide and the dihydroceramide (DH ceramide) were performed. In this case, the control was treated with distilled water instead of each of the palmitoyl serinol and valproyl serinol samples.

The results obtained by the method are shown in FIGS. 9 and 10 below.

3. Confirmation of Liquid Crystal Formation

Formation of liquid crystals by each of the samples (Examples and Comparative Examples) was confirmed using a polarizing microscope (NIKON ECLIPSE 80i (Nikon, Japan)). In this case, the control materials, that is, a formulation forming no Maltese cross liquid crystals (Comparative Example 1) and Vaseline, were used as Controls A and B, respectively.

Also, after the liquid crystals of Examples and Comparative Examples were stored at 25° C. (room temperature), 30° C., and 50° C. for 30 days in thermostatic baths, changes in structures of the liquid crystals were confirmed.

The results are shown in FIGS. 1 to 5 below.

4. Confirmation of Presence of Developmental Toxicity in Zebrafish

It was confirmed whether each of palmitoyl serinol and valproyl serinol showed the developmental toxicity in a zebrafish. In this case, a 1% DMSO aqueous solution that was a stock solution was used as the control material.

Specifically, each of the samples was prepared at concentrations of 1, 10, and 100 µg/mL using the stock solution. After each of the samples was adjusted to these concentrations, fertilized eggs of the zebrafish were exposed to each of the samples for 4 hours. 24 hours after fertilization (20 hours after the exposure to each of the samples) and 48 hours after fertilization (44 hours after the exposure to each of the samples), it was judged whether or not the samples were toxic overall. In this case, the toxicity was evaluated based on the indicators divided into eight categories (Normal Development; Death; Coagulated Egg; Necrotic Tissue; Eye Development Alteration; Edema (Pericardial Edema); Tail Formation; and General Retardation).

As a result, it was confirmed that the fertilized eggs of the zebrafish developed normally in different concentrations of the samples of palmitoyl serinol and valproyl serinol. That is, it was confirmed that the serinol-based compound according to the present invention had no developmental toxicity.

5. Confirmation of Efficacy as Cannabinoid Type 1 Receptor Agonist

The efficacy of each of palmitoyl serinol and valproyl serinol on the inhibition of cAMP generation was confirmed by means of the antagonism using CHO cells in which the cannabinoid type 1 receptor was overexpressed. In this case, arachidonyl-2-chloroethylamide (ACEA) known as the cannabinoid type 1 receptor agonist was used as the control material.

Specifically, CHO cells in which the cannabinoid type 1 receptor was overexpressed were purchased from ChanTest Corp., and cultured in an F-12 medium (Gibco-BRL) supplemented with 10% fetal bovine serum (FBS; Gibco-BRL). The cells were seeded in a 96-well dish, cultured for 24 hours, and then treated at concentrations of 0, 0.781, 1.562, 3.125, 6.25, 12.5, 25, and 50 µM (0.1% DMSO in PBS). The cells were treated with 10 µM forskolin (Sigma) to induce the generation of cAMP by adenylyl cyclase in the cells. The intracellular cAMP concentration was measured using a HTRF cAMP assay kit purchased from Cisbio US Inc. The cells were lysed in a lysis buffer in the kit, and then treated at room temperature for 2 hours with anti-cAMP cryptate conjugate and cAMP-d2 in the kit according to the manufacturer's manual. Thereafter, the fluorescences at 665 nm and 620 nm were measured, and calibrated at a ratio of 665 nm/620 nm. Then, the intracellular cAMP concentration was measured using a standard curve.

The results are shown in FIG. 8 below.

Examples 1 to 6

Compositions for skin external application were prepared according to the following method using the components of the following Table 1.

(1) All aqueous-phase components were mixed.

(2) All oily components were mixed, and the resulting mixture was heated and dissolved at 70° C. Thereafter, the aqueous-phase components were added to the mixture, and emulsified for 3 minutes using a homomixer to prepare composition for skin external application (an oil-in-water cosmetic composition).

Comparative Examples 1 and 2

Compositions for skin external application were prepared according to the method of Example 1 using the components of the following Table 1.

TABLE 1

| % by weight | Components (Material Name) | Examples 1 | 2 | 3 | 4 | 5 | 6 | Comparative Examples 1 | 2 |
|---|---|---|---|---|---|---|---|---|---|
| Oil | Palmitoyl serinol | 0.1 | 0.1 | 0.1 | 0.6 | 0.6 | — | — | — |
| | Valproyl serinol | — | — | — | — | — | 0.1 | — | — |
| | Ceramide 3 | — | 00.1 | — | — | 00.1 | — | — | — |
| | PC-9S | — | — | 0.6 | — | — | — | — | 0.1 |
| | Phytosterol sterol | 0.5 | 0.5 | 0.5 | 0.5 | 0.5 | 0.5 | 0.5 | 0.5 |
| | Stearic acid | 1.5 | 1.5 | 1.5 | 1.5 | 1.5 | 1.5 | 1.5 | 1.5 |
| | Cetylstearyl alcohol | 3.0 | 3.0 | 3.0 | 3.0 | 3.0 | 3.0 | 3.0 | 3.0 |
| | Caprylic/capric triglyceride | 10.0 | 10.0 | 10.0 | 10.0 | 10.0 | 10.0 | 10.0 | 10.0 |
| Aqueous phase | Water | To 100 | To 100 | To 100 | To 100 | To 100 | To 100 | To 100 | To 100 |
| | Glycerine | 1.5 | 1.5 | 1.5 | 1.5 | 1.5 | 1.5 | 1.5 | 1.5 |
| | Polyglyceryl-10 distearate | 2.0 | 2.0 | 2.0 | 2.0 | 2.0 | 2.0 | 2.0 | 2.0 |
| | Glyceryl stearate | 3.5 | 3.5 | 3.5 | 3.5 | 3.5 | 3.5 | 3.5 | 3.5 |

As shown in the drawings below, the stably formed Maltese cross liquid crystals were confirmed in the composition for skin external application according to the present invention (see FIGS. 1 to 5). In particular, it was confirmed that the liquid crystals were stably preserved during the long-term storage in the case of Examples including the ceramide. In contrast, the Maltese cross liquid crystals were not observed in the case of Comparative Examples.

Also, it can be seen that the composition for skin external application according to the present invention gave an immediate skin moisturizing effect after the composition for skin external application was applied on the skin (see FIG. 7). However, it can be seen that Control A (Comparative Example 1) in which the Maltese cross liquid crystal structure was not observed had an inferior moisturizing effect, compared to the composition of the present invention. It can be seen that Vaseline used as Control B showed an insignificant level of the immediate moisturizing effect on the skin, but tended to increase moisture in the skin with the elapse of time. These results are expected from the fact that an oil-rich protective film was formed on the skin when Vaseline was used as Control B.

In addition, the composition for skin external application according to the present invention had an increased transepidermal water loss, which was significantly lower than those of Control A (Comparative Example 1) and Control B (Vaseline) used as the control materials (see FIG. 6).

Moreover, the composition for skin external application according to the present invention acted as the cannabinoid type 1 receptor agonist to suppress the adenylyl cyclase activity and effectively suppress the intracellular cAMP generation. As shown in FIG. 8, it can be seen that, when the cells were treated with each of the serinol-based compounds, the cAMP concentration decreased in a manner dependent on the concentration of each of the serinol-based compounds. This indicates that the composition for skin external application according to the present invention was effective as the cannabinoid type 1 receptor agonist. Also, it was confirmed that this suppressive effect corresponded to the effect greater than or equal to that of ACEA well-known as the cannabinoid type 1 receptor agonist.

Further, it was confirmed that the composition for skin external application according to the present invention remarkably improved the biosynthesis of the long-chain ceramide and dihydroceramide having an intracellular N-acyl chain length of 14 carbon atoms (see FIGS. 9 and 10 below). Such an effect was shown to be more effective for the biosynthesis of the long-chain ceramide and dihydroceramide having an N-acyl chain length of 16 or 24 carbon atoms.

In particular, since the dihydroceramide was one of the metabolites involved in the metabolism of ceramide newly generated in the skin, an effect of increasing the biosynthesis of dihydroceramide may mean that it is possible to enhance the skin barrier functions as well as improve the underlying functions of the damaged or attenuated skin. Therefore, the composition for skin external application according to the present invention is expected to exhibit an outstanding effect in improving and enhancing the original functions of the skin.

Although the present invention has been described with reference to certain subject matters and limited examples thereof, it should be understood that the subject matters and limited examples described herein are provided to aid in understanding the present invention more comprehensively, but are not intended to limit the present invention. Therefore, it will be apparent to those skilled in the art to which the present invention pertains that various changes and modifications can be made from the detailed description of the present invention.

Thus, the scope of the present invention is not intended to be limited to the examples described herein, and thus the appended claims, and all types of equivalents or equivalent modifications thereof fall within the scope of the present invention.

The invention claimed is:

1. A composition for skin external application comprising a serinol-based compound selected from the group consisting of palmitoyl serinol and valproyl serinol, a sterol-based compound, a higher fatty acid, and a higher fatty acid alcohol, wherein the composition for skin external application forms Maltese cross liquid crystals, and wherein the composition for skin external application comprises 1 to 10 parts by weight of the sterol-based compound, 5 to 30 parts by weight of the higher fatty acid, and 10 to 50 parts by weight of the higher fatty acid alcohol, based on 1 part by weight of the serinol-based compound.

2. The composition for skin external application of claim 1, wherein the composition for skin external application further comprises a ceramide selected from ceramide 1, ceramide 3, ceramide 3B, ceramide 4, ceramide 6, myristoyl/palmitoyl oxostearamide/arachamide MEA, hydroxypropylbispalmitamide MEA, hydroxypropylbispalmitamide MEA, and dihydroxyisopropyl palmoylpalmamide.

3. The composition for skin external application of claim 2, wherein the ceramide is included at 0.01 to 10 parts by weight, based on 1 part by weight of the serinol-based compound.

4. The composition for skin external application of claim 1, wherein the composition for skin external application is a cosmetic composition for moisturizing the skin or strengthening a skin barrier.

5. The composition for skin external application of claim 1, wherein the composition for skin external application is a cosmetic composition for improving a skin disease.

6. The composition for skin external application of claim 1, wherein the composition for skin external application is a pharmaceutical composition for treating or improving a skin disease.

7. The composition for skin external application of claim 6, wherein the skin disease is atopic dermatitis.

8. The composition for skin external application of claim 1, wherein the composition for skin external application is a pharmaceutical composition for treating or improving a mental disorder associated with a skin disease.

9. The composition for skin external application of claim 8, wherein the mental disorder is attention deficit hyperactivity disorder, intermittent explosive disorder, depression, or conduct disorder.

10. The composition for skin external application of claim 1, wherein the composition for skin external application is a pharmaceutical composition for treating or improving a mental disorder.

* * * * *